US008021358B2

(12) United States Patent
Doyle et al.

(10) Patent No.: US 8,021,358 B2
(45) Date of Patent: Sep. 20, 2011

(54) SURGICAL TOOL KIT

(75) Inventors: Mark C. Doyle, San Diego, CA (US); Jimmy C. Caputo, Carlsbad, CA (US)

(73) Assignee: CareFusion 2200, Inc., San Diego, CA (US)

( * ) Notice: Subject to any disclaimer, the term of this patent is extended or adjusted under 35 U.S.C. 154(b) by 1106 days.

(21) Appl. No.: 11/775,170

(22) Filed: Jul. 9, 2007

(65) Prior Publication Data
US 2008/0015552 A1 Jan. 17, 2008

Related U.S. Application Data

(63) Continuation of application No. 10/870,084, filed on Jun. 16, 2004, now Pat. No. 7,241,290.

(51) Int. Cl.
*A61B 17/00* (2006.01)
(52) U.S. Cl. .......................................... 606/1; 81/177.4
(58) Field of Classification Search ..... 606/1; 81/177.4, 81/177.6, 490
See application file for complete search history.

(56) References Cited

U.S. PATENT DOCUMENTS

| 4,572,038 A | 2/1986 | Graham |
| 4,848,338 A | 7/1989 | De Satnick et al. |
| 5,456,684 A | 10/1995 | Schmidt et al. |
| 5,496,317 A | 3/1996 | Goble et al. |
| 5,575,799 A | 11/1996 | Bolanos et al. |
| 5,599,350 A | 2/1997 | Schulze et al. |
| 5,611,813 A | 3/1997 | Lichtman |
| 5,618,307 A | 4/1997 | Donlon et al. |
| 5,620,459 A | 4/1997 | Lichtman |
| 5,700,261 A | 12/1997 | Brinkerhoff |
| 5,746,740 A | 5/1998 | Nicholas |
| 5,746,759 A | 5/1998 | Meade et al. |
| 5,752,972 A | 5/1998 | Hoogeboom |
| 5,791,231 A | 8/1998 | Cohn et al. |
| 5,797,941 A | 8/1998 | Schulze et al. |
| 5,820,623 A | 10/1998 | Ng |
| 5,876,410 A | 3/1999 | Petillo |
| 5,931,832 A | 8/1999 | Jensen |
| 6,024,695 A | 2/2000 | Taylor et al. |
| 6,099,536 A | 8/2000 | Petillo |
| 6,102,909 A | 8/2000 | Chen et al. |

(Continued)

FOREIGN PATENT DOCUMENTS

DE 10149421 A 4/2003

(Continued)

OTHER PUBLICATIONS

International Search Report and Written Opinion dated Nov. 17, 2005 in PCT/US2005/020731.

(Continued)

*Primary Examiner* — Roy D Gibson
(74) *Attorney, Agent, or Firm* — Arent Fox LLP

(57) ABSTRACT

A tool kit for interchanging tools within an at least partially closed area is provided. The tool kit includes at least one tool, each tool being preferably provided within a tubular housing, and adapted to pivot out from the tool kit so that they can be attached to a receiving tool. The tool is designed to be returned to the tool kit after use, and if desired, switched with a different tool. In one embodiment, a surgical system permitting surgical tools to be interchanged within a patient's body is provided. A method of interchanging surgical tools within a patient's body is also provided.

19 Claims, 11 Drawing Sheets

U.S. PATENT DOCUMENTS

| | | | |
|---|---|---|---|
| 6,179,837 B1 | 1/2001 | Hooven | |
| 6,197,017 B1 | 3/2001 | Brock et al. | |
| 6,223,100 B1 | 4/2001 | Green | |
| 6,296,635 B1 | 10/2001 | Smith et al. | |
| 6,309,397 B1 | 10/2001 | Julian et al. | |
| 6,346,072 B1 | 2/2002 | Cooper | |
| 6,361,534 B1 | 3/2002 | Chen et al. | |
| 6,371,952 B1 | 4/2002 | Madhani et al. | |
| 6,391,029 B1 | 5/2002 | Hooven et al. | |
| 6,398,726 B1 | 6/2002 | Ramans et al. | |
| 6,424,885 B1 | 7/2002 | Niemeyer et al. | |
| 6,432,112 B2 | 8/2002 | Brock et al. | |
| 6,434,329 B1 | 8/2002 | Dube et al. | |
| 6,441,577 B2 | 8/2002 | Blumenkranz et al. | |
| 6,468,265 B1 | 10/2002 | Evans et al. | |
| 6,488,265 B2 | 12/2002 | Laskaris et al. | |
| 6,491,691 B1 | 12/2002 | Morley et al. | |
| 6,554,844 B2 | 4/2003 | Lee et al. | |
| 6,574,355 B2 | 6/2003 | Green | |
| 6,607,475 B2 | 8/2003 | Doyle et al. | |
| 6,620,174 B2 | 9/2003 | Jensen et al. | |
| 6,622,980 B2 | 9/2003 | Boucher et al. | |
| 6,665,554 B1 | 12/2003 | Charles et al. | |
| 6,671,581 B2 | 12/2003 | Niemeyer et al. | |
| 6,676,669 B2 | 1/2004 | Charles et al. | |
| 6,676,684 B1 | 1/2004 | Morley et al. | |
| 6,692,485 B1 | 2/2004 | Brock et al. | |
| 6,702,805 B1 | 3/2004 | Stuart | |
| 6,723,087 B2 | 4/2004 | O'Neill et al. | |
| 6,723,106 B1 | 4/2004 | Charles et al. | |
| 6,731,988 B1 | 5/2004 | Green | |
| 6,746,443 B1 | 6/2004 | Morley et al. | |
| 6,755,338 B2 | 6/2004 | Hahnen et al. | |
| 6,764,445 B2 | 7/2004 | Ramans et al. | |
| 6,770,081 B1 | 8/2004 | Cooper et al. | |
| 6,776,783 B1 | 8/2004 | Frantzen et al. | |
| 6,783,524 B2 | 8/2004 | Anderson et al. | |
| 6,786,896 B1 | 9/2004 | Madhani et al. | |
| 6,788,018 B1 | 9/2004 | Blumenkranz | |
| 6,788,999 B2 | 9/2004 | Green | |
| 6,817,974 B2 | 11/2004 | Cooper et al. | |
| 6,827,725 B2 | 12/2004 | Batchelor et al. | |
| 6,830,174 B2 | 12/2004 | Hillstead et al. | |
| 6,840,938 B1 | 1/2005 | Morley et al. | |
| 6,843,793 B2 | 1/2005 | Brock et al. | |
| 6,850,817 B1 | 2/2005 | Green | |
| 6,860,878 B2 | 3/2005 | Brock | |
| 6,866,671 B2 | 3/2005 | Tierney et al. | |
| 6,879,880 B2 | 4/2005 | Nowlin et al. | |
| 6,936,042 B2 | 8/2005 | Wallace et al. | |
| 6,963,792 B1 | 11/2005 | Green | |
| 6,991,627 B2 | 1/2006 | Madhani et al. | |
| 6,994,708 B2 | 2/2006 | Manzo | |
| 6,999,852 B2 | 2/2006 | Green | |
| 7,006,895 B2 | 2/2006 | Green | |
| 7,048,745 B2 | 5/2006 | Tierney et al. | |
| 7,063,697 B2 | 6/2006 | Slater | |
| 7,083,615 B2 | 8/2006 | Peterson et al. | |
| 7,083,618 B2 | 8/2006 | Couture et al. | |
| 7,090,683 B2 | 8/2006 | Brock et al. | |
| 7,101,371 B2 | 9/2006 | Dycus et al. | |
| 7,107,124 B2 | 9/2006 | Green | |
| 7,108,688 B2 | 9/2006 | Jensen | |
| 7,125,403 B2 | 10/2006 | Julian et al. | |
| 7,155,315 B2 | 12/2006 | Niemeyer et al. | |
| 7,155,316 B2 | 12/2006 | Sutherland et al. | |
| 7,169,141 B2 | 1/2007 | Brock et al. | |
| 7,204,844 B2 | 4/2007 | Jensen et al. | |
| 7,246,734 B2 | 7/2007 | Shelton, IV | |
| 7,248,944 B2 | 7/2007 | Green | |
| 7,250,028 B2 | 7/2007 | Julian et al. | |
| 7,252,660 B2 | 8/2007 | Kunz | |
| 7,276,065 B2 | 10/2007 | Morley et al. | |
| 7,297,142 B2 | 11/2007 | Brock | |
| 7,306,597 B2 | 12/2007 | Manzo | |
| 7,316,681 B2 | 1/2008 | Madhani et al. | |
| 7,320,700 B2 | 1/2008 | Cooper et al. | |
| 7,600,451 B2 * | 10/2009 | Lechot et al. | 81/62 |
| 2002/0042620 A1 | 4/2002 | Julian et al. | |
| 2002/0120252 A1 | 8/2002 | Brock et al. | |
| 2003/0083673 A1 | 5/2003 | Tierney et al. | |
| 2003/0109877 A1 | 6/2003 | Morley et al. | |
| 2003/0135204 A1 | 7/2003 | Lee et al. | |
| 2003/0216715 A1 | 11/2003 | Moll et al. | |
| 2003/0236549 A1 | 12/2003 | Bonadio et al. | |
| 2004/0039485 A1 | 2/2004 | Niemeyer et al. | |
| 2004/0193146 A1 | 9/2004 | Lee et al. | |
| 2005/0021018 A1 | 1/2005 | Anderson et al. | |
| 2005/0149003 A1 | 7/2005 | Tierney et al. | |
| 2005/0215983 A1 | 9/2005 | Brock | |
| 2005/0216033 A1 | 9/2005 | Lee et al. | |
| 2005/0228440 A1 | 10/2005 | Brock et al. | |
| 2005/0240178 A1 | 10/2005 | Morley et al. | |
| 2007/0012135 A1 | 1/2007 | Tierney et al. | |
| 2007/0021776 A1 | 1/2007 | Jensen et al. | |
| 2007/0088340 A1 | 4/2007 | Brock et al. | |
| 2007/0093792 A1 | 4/2007 | Julian et al. | |
| 2007/0123855 A1 | 5/2007 | Morley et al. | |
| 2007/0233052 A1 | 10/2007 | Brock | |
| 2008/0033453 A1 | 2/2008 | Brock | |

FOREIGN PATENT DOCUMENTS

| | | | |
|---|---|---|---|
| GB | 2343646 A | 5/2000 | |

OTHER PUBLICATIONS

International Preliminary Report on Patentability dated Dec. 20, 2006 in PCT/US2005/020731.

* cited by examiner

SURGICAL TOOL KIT

RELATED APPLICATIONS

This application is a continuation of U.S. application Ser. No. 10/870,084, filed Jun. 16, 2004 now U.S. Pat. No. 7,241,290, which is incorporated herein by reference in its entirety.

BACKGROUND OF THE INVENTION

1. Field of the Invention

The invention relates generally to surgical instruments. More particularly, the invention relates to a tool kit for use in minimally invasive surgical procedures.

2. Description of the Related Art

Current laparoscopic surgical tools are limited in accessibility of certain regions of the human body. Existing tools can perform invasive surgery without making a substantial incision, but these tools are incapable of bending within the body to reach, for example, the backside of the human heart.

Additionally, existing tools rely on use of cables to manipulate the surgical tip of the tool. These tools have the disadvantage of requiring extensive sterilization of the internal components. The cleaning of internal metal cables can be a lengthy and expensive process. This process must be repeated prior to each procedure. Alternatively, disposable components may be used with a substantial increase in recurring costs.

Furthermore, current laparoscopic surgical systems are limited because the tools used to perform various functions within the body have to be changed outside the body. The entire system must be removed from the body, the tool changed outside of the body, and then the system be reinserted into the body. Alternatively, additional incisions are made in the patient's body through which additional surgical tools are inserted. This makes the surgical procedure more complex, and patient recovery time is increased.

Accordingly, there is a need for a laparoscopic surgical system that permits a surgical tool to be changed within the body.

There is also a need for a tool kit that permits a tool to be changed within a closed area.

SUMMARY OF THE INVENTION

Disclosed herein is a tool kit comprising a housing having at least one attachment point; at least one tool holder having an attachment element, wherein said attachment element is adapted to attach said tool holder to said attachment point on said housing; at least one tool adapted to be removably secured to said tool holder; wherein said tool is also adapted to be connected to a manipulator for use within a generally closed or confined area, and wherein when said tool is connected to said manipulator, an operator of said manipulator can exchange said connected tool for a second tool without first removing said manipulator from said generally closed or confined area; and wherein when said tool is placed inside said tool holder, said tool cannot be removed therefrom unless said tool is properly connected to said manipulator, and when said tool is properly connected to said manipulator, said tool cannot be released therefrom unless said tool is properly secured into said tool holder.

Also disclosed herein is a tool kit comprising a housing having an opening and at least one attachment point within said opening, wherein said housing comprises a generally cylindrical body; at least one tool holder having an attachment element, wherein said attachment element is adapted to attach said tool holders to said attachment point on said housing, and wherein said tool holder is adapted to fit within said opening so that when said tool holder is within said opening the diameter of said housing is not increased; at least one tool adapted to be removably secured to said tool holder; wherein said tool is also adapted to be connected to a manipulator for use within a generally closed or confined area, and wherein when said tool is connected to said manipulator, an operator of said manipulator can exchange said connected tool for a second tool without first removing said manipulator from said generally closed or confined area; and wherein when said tool is placed inside said tool holder, said tool cannot be removed therefrom unless said tool is properly connected to said manipulator, and when said tool is properly connected to said manipulator, said tool cannot be released therefrom unless said tool is properly secured into said tool holder.

Further, disclosed herein is a tool holder comprising a body, defining a cavity within said body, said cavity configured to hold a tool; a projection within said cavity set at a distance away from a wall of said body; a cam; at least one keyway configured to allow a tine of a tool receiving device to pass therethrough; and an attachment element for attachment of said tool holder to a tool kit.

In addition, disclosed herein is a tool kit comprising at least one tool; means for holding said tool; means for attaching said means for holding a tool to said tool kit; and means for attaching said tool kit to a tool kit receiving device.

Disclosed herein is also a method of interchanging tools within a generally closed or confined area comprising: inserting a tool kit into said closed area, wherein said tool kit comprises a plurality of tools each held within a tool holder; attaching a manipulator to a first of said plurality of tools held within a first tool holder; removing said first tool from said first tool holder; manipulating said first tool; replacing said first tool in said first tool holder; attaching said manipulator to a second of said plurality of tools held within a second tool holder; and manipulating said second tool; wherein said manipulator is not removed from said generally closed or confined area during steps b) through f).

DETAILED DESCRIPTION OF THE PREFERRED EMBODIMENT

Figure 1:
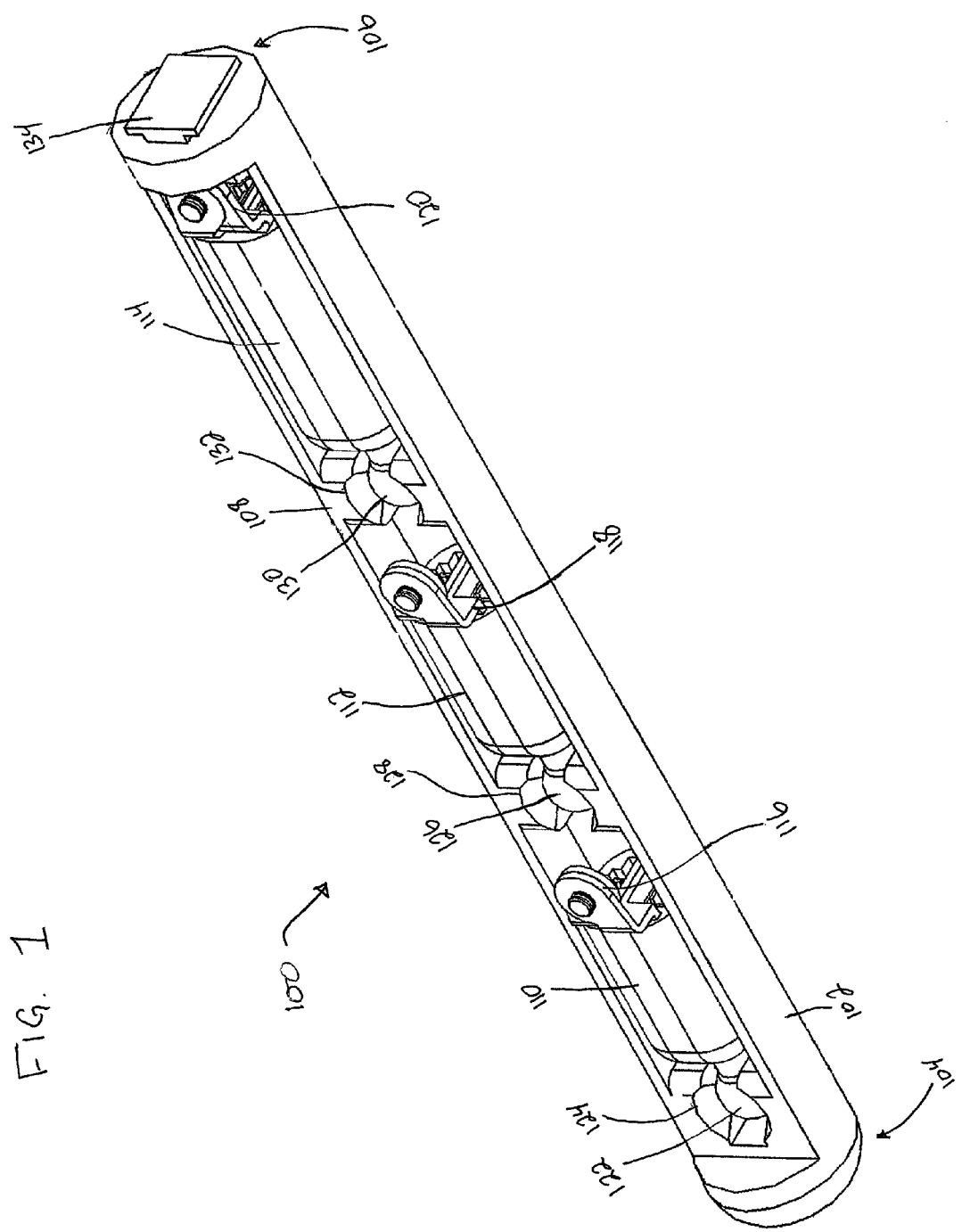
FIG. 1 is a perspective view of a tool kit in accordance with one embodiment of the present invention.

Aspects of the present disclosure relate to a system of interchangeable tools for use within a closed area. In general, disclosed herein is a holder which comprises one or more tools attached thereto. The holder and the attached tools are so configured that they can be inserted into a closed area and easily manipulated therein. Examples of the closed area include inside the body of a patient, as in during laparoscopic or arthroscopic surgery, or inside of a device or a mechanical object, as in during maintenance or repair of the interior of said device or mechanical object.

In certain embodiments, the tools are configured to be attached to the distal end of a manipulator, which itself is configured to receive the tools. The distal end of the manipulator can itself be inserted into the closed area. The distal end of the manipulator can be controlled by an operator at a proximal end, i.e., the end closest to the operator. Within the closed area, the operator can choose a desired tool from a selection of tools on the holder and attach it to the distal end of the manipulator. After the operator has used the tool in a desired fashion, the operator can then return the just-used tool to the holder, obtain a second tool from the holder, attach it to the distal end of the manipulator, and use the second tool. The operator can repeat this process as many times as the operator desires, thereby interchanging the tool used inside the closed area without having the need to withdraw the manipulator from the closed area. As described in detail below, this system is designed for use, for example, in laparoscopic surgery. The tools are various surgical tools used within the patient's body. The tools in the holder are inserted into the body. During surgery, the surgeon can use and exchange tools without the need to remove the manipulator or the tools themselves from the body. This represents a significant improvement over existing methods and devices.

A "manipulator" as used herein refers to a device that at its proximal end comprises a set of controls to be used by an operator and at its distal end comprises means for holding and operating a tool, referred to herein as the "tool receiving device." The controls allow the operator to move the tool receiving device within the generally closed or confined area, and operate the tool as intended. The tool receiving device is adapted to receive tools interchangeably and can cause a variety of different tools to operate in their intended purpose. Examples of a manipulator include any of a variety of laparoscopic or arthroscopic surgical tools available on the market for use by surgeons, or the device described in U.S. Pat. No. 6,607,475. The tool receiving device of a manipulator is adapted to enter a generally closed or confined area through a small opening, such as a small hole in a mechanical device or a small incision in a human body.

As used herein, "proximal" refers to the part of the device that remains outside of the closed area, closest to the operator. "Distal" refers to the end inserted into the closed area, farthest away from the operator. The proximal and distal ends are preferably in communication with each other, such as fluid communication, electrical communication, communication by cables, and the like. Such communication can occur, for example, through a catheter or cannula, which houses the lines used for such communication. The catheter or cannula is preferably a tube or other substantially cylindrical hollow object. In some embodiments, the catheter or cannula does not house any lines for communication between the proximal and distal ends. In these embodiments, the catheter or cannula is used for placing an object, located substantially at the distal end of the catheter or cannula, inside the closed area for further manipulation.

During the operation of the devices described herein, the catheter or cannula (hereinafter referred to simply as "cannula") is inserted into a generally closed or confined area where the tools are to be used such that its proximal end remains outside the closed area while the distal end remains inside the closed area. In the context of surgical procedures, the cannula is inserted into the patient's body such that its proximal end remains outside the body while the distal end remains inside the body. This allows the operator, e.g. a surgeon, to access the interior of the closed area, e.g., a patient's body, using the cannula, thereby eliminating the need for "open" surgical procedures. Only a small incision is needed to insert the cannula, and the various surgical instruments are inserted, and the procedures performed, through the cannula.

The instruments or tools described herein are capable of being attached to the distal end of the manipulator in a number of different ways. For instance, in some embodiments the tools are attached magnetically, while in other embodiments the tools may clip on to the distal end of the manipulator. Additional details on the attachment of the tools is provided below.

The manipulator, which is used to position and maneuver the tools within the confined space, can be a hydraulic, pneumatic, robotic, standard surgical, minimal invasive surgery (MIS), electrical, or mechanical device, or a device comprising a combination of any of these systems. Any system that can be used to position and manipulate the tools is contemplated.

The tools and the methods described herein perform a number of different functions. Examples include tools that are used as graspers, scissors, blades, screw drivers, such as flathead or Phillips head, drill bits, wrenches, including Allen wrenches, soldering irons, ultrasonic cutters, suture drivers, clip drivers, suction/irrigation devices, cauterization devices, needles, catheters, tissue stabilizers, nerve/vessel locators, radiological devices and the like.

With reference to FIGS. 1-11, certain embodiments of a system and method for interchanging tools within a generally closed or confined area are shown. The devices and methods herein are readily applicable to a wide variety of embodiments wherein it is desirable to interchange tools in closed areas, and all such applications are contemplated by the present inventors. Adaptation of the devices and methods disclosed herein to accomplish procedures such as the foregoing will be apparent to those of skill in the art in view of the disclosure herein.

Tool Kit

Aspects of the present invention provide a tool kit system that allows an operator to insert a variety of different tools through a relatively small opening into a generally closed or confined area, use the tools and interchange them as needed without the need to withdraw either the tool kit or the manipulator to which the tools are attached, and once the work is done, withdraw the tool kit from the closed or confined area. Thus, in some embodiments, the tool kits described herein provide a number of tools, each of which is held within a tool holder. The several tool holders are attached to a housing. During the insertion of the tool kit into the generally closed or confined area, the tool holders are nestled within the housing to maximize space efficiency and allow for the tool kit to fit through the small opening of the generally closed or confined area. Once inside the generally closed or confined area, the operator can pivot the tool holders away from the housing to expose the tools to the manipulator to which the tools are to be attached. After the operator is done with the particular tool, the operator can then return the tool to its holder and nestle the holder back inside the housing to allow the tool kit to be extracted from inside the generally closed or confined area through the small opening.

As shown in FIG. 1, one embodiment of a system for interchanging tools within a generally closed or confined area is provided. The tool kit 100 includes a housing 102, also referred to herein as a holder, having a distal end 104 and a proximal end 106. The housing 102 includes an opening 108, in which a plurality of tool holders 110, 112, 114 are provided. Embodiments of the tool kit 100 include those in which only one tool holder 110 is included with each tool kit 100. In other embodiments, two or more tool holders 110 are included. The embodiment shown in FIG. 1 comprises three tool holders. Each tool holder 110, 112, 114 can contain a tool 116, 118, 120, as described below.

The tool holders 110, 112, 114 are configured such that they fit within the housing 102 during the insertion of the tool kit 100 into the confined area, or during the extraction therefrom, and yet can pivot away from the housing 102 to present the tools for attachment to the manipulator. This arrangement creates maximum space efficiency that allows an easy fit through a small opening during insertion and removal.

The tool holders 110, 112, 114 can include an attachment element 122, 126, 130 which is received in a corresponding attachment point 124, 128, 132 provided on the tool kit 100. The combination of the attachment element 122, 126, 130 and the attachment point 124, 128, 132 create a hinge that allows the tool holders 110, 112, 114 to rotate outwardly from a resting position, as in 114 in FIG. 2, to a semi-extended position, as in 110 in FIG. 2, to a fully extended position, as in 112 in FIG. 2. Based on the angle of approach, the operator can rotate the tool holders 110, 112, 114 to a semi-extended position, a fully extended position, or any desired position in between a resting position and a fully extended position. A position of the tool holder 110, 112, 114 other than a resting position, e.g., a semi-extended position or a fully extended position, is referred to herein as "an extended position."

The way by which the attachment element 122, 126, 130 is attached to the attachment point 124, 128, 132 generally permits the tool holders 110, 112, 114 to pivot outwardly from a resting position to an extended position. In one embodiment, the attachment element is flexible enough to allow the tool holder 110, 112, 114 to be pivoted away from the housing 102, i.e., from a resting position to an extended position, after being manipulated into such an extended position by the operator, and yet is stiff enough to retain the extended position away from the housing 102 once the operator has positioned the tool holder 110, 112, 114 in that extended position.

In one embodiment, the attachment element 122, 126, 130 is a generally spherical ball, which fits within the attachment point 124, 128, 132, which in turn is a generally hollow sphere or socket, having an opening to receive the attachment element 122, 126, 130. In another embodiment, the attachment element 122, 126, 130 is attached to the attachment point 124, 128, 132 by a pin. In still another embodiment, the attachment element 122, 126, 130 comprises a pin on either side that fit within, or snap into, a corresponding hole or dimple on the attachment point 124, 128, 132. In yet another embodiment, the element 122, 126, 130 may be a pivot, such as a cylindrical or spherical pivot. In some embodiments, the pivot is a spring pivot which permits release and return to the resting position. Other modes of attachment known in the art can also be used. The attachment point 124, 128, 132 can be an opening in the housing 102, which permits the attachment element 122, 126, 130 to rest and/or pivot therein. In other embodiments, the attachment point 124, 128, 132 can be a point to which the attachment element 122, 126, 130 is snapped, glued, welded, soldered, or otherwise attached.

To place the tool kit 100 inside the generally closed or confined area, the tool kit 100 is attached to a tool kit receiving device (not shown). The tool kit receiving device can be introduced into the generally closed or confined area through the same small opening through which the manipulator is introduced, or it can be introduced through a separate small opening. The tool kit receiving device can also be the same as the manipulator. The tool kit receiving device can be a rod, made out of wood, metal, plastic, and the like, a flexible hose, or tube. In the context of a surgical system, the receiving device can be a cannula. The cannula can be the same cannula that moves the distal end of the manipulator, or it can be a separate cannula.

Referring again to FIG. 1, the tool kit 100 can include an attachment element 134 at its proximal end 106 for attaching the tool kit 100 to the tool kit receiving device. In one embodiment, the attachment element 134 is a dovetail connection. In other embodiments, the tool kit 100 can snap onto the tool kit receiving device. In further embodiments, the tool kit 100 and the tool kit receiving device can be attached magnetically. In some of these embodiments, the attachment element 134 can be a magnet, or an electromagnetic device that can be magnetized upon the introduction of electrical current. In yet other embodiments, the tool kit 100 can be attached to the tool kit receiving device by a pin. In other embodiments, the attachment element 134 can be a hook, or a loop for receiving a hook. Other methods of releasably attaching the took kit 100 to a tool kit receiving device can be used.

In certain embodiments, the tool kit 100 can be an integral part of the cannula. In these embodiments, the tool kit 100 need not include an attachment element 134. Further, in these embodiments, an operator may include the arrangement of the tools he or she desires in the tool kit 100 prior to the insertion of the cannula into the closed area.

The tool kit receiving device, e.g., the cannula, is used for positioning the tool kit 100 within the generally closed or confined area. In some embodiments, the tool kit receiving device is used to hold the tool kit 100 in place for the duration of its use within the generally closed or confined area. In other embodiments, the tool kit receiving device is used to place the tool kit 100 within the generally closed or confined area, and subsequent to this, the tool kit receiving device is withdrawn. In these embodiments, the tool kit 100 is attached, using attachment element 134, to a feature within the generally closed or confined area, for example, another part of the instrument within that area, such as another cannula or the manipulator, or a solid object, such as a part of the machinery, within that area. Thus, for example, the tool kit 100 can be magnetic, in which case it can be attached to a metal surface suitably located within the closed area. The attachment element 134 can also be a hook, which can then be hooked to a suitable place within the closed or confined area. Other methods of attachment, such as Velcro®, adhesives, hangers, and the like, are also within the scope of the present disclosure.

The tool kit receiving device and the tool kit 100 are configured such that they can be inserted into the generally closed or confined area with relative ease. In the context of a surgical procedure, the surgeon prefers to make a small incision through which the tool kit receiving device and the tool kit 100 can be inserted into the patient's body. In the context of repairs to a mechanical device, the tool kit receiving device and the tool kit 100 can be inserted to the inside of the mechanical device through a small opening. Therefore, it is desirable that the respective widths of the tool kit receiving device and the tool kit 100 are similar. Similarity of the widths of the two components prevents injury to the patient's tissue, e.g., from objects of various widths passing through the small incision, or injury to the instrument or the mechanical device to be repaired.

In some preferred embodiments, including that shown in FIG. 1, the tool kit receiving device is generally cylindrical, and the housing 102 of the tool kit 100 has about the same outer diameter as the outer diameter of the generally cylindrical tool kit receiving device. In other embodiments, the housing 102 has an outer diameter less than or greater than the tool kit receiving device. In other embodiments, the tool kit receiving device is not cylindrical. The actual dimensions of the tool kit can vary depending its intended use. In some embodiments, where the tool kit receiving device and the tool kit 100 have different diameters, the transition area between the two components is gently sloped so as to avoid contacting sharp edges of the component having the larger diameter with the perimeter of the hole through which the tool kit receiving device and the tool kit 100 are being inserted, thereby minimizing any injury such insertion may cause.

In some embodiments, such as in a system described in U.S. Pat. No. 6,607,475, the cannula houses the lines used for hydraulic communication. The manipulator is located at the end of the cannula. In some embodiments, the tool kit 100 is attached to the same cannula to which the manipulator device is also attached. Therefore, the manipulator, which comprises a distal end to which the tools of the tool kit 100 is attached, and the tool kit 100, are introduced into the closed area via a single entry point. In some of these embodiments, the tool kit 100 forms a portion of the cannula itself.

In other embodiments, the tool kit 100 is attached to a different cannula than the manipulator. In these embodiments, the cannula holding the tool kit 100 serves to place the tool kit 100 in a convenient place, where the operator can access the tools within the tool kit 100 by the distal end of the manipulator. In these embodiments, the cannula may or may not house hydraulic communication lines.

In certain embodiments, the distal end of the manipulator ends in a tool receiving device, such as a pair of tines, or equivalents thereof, to which the tools described herein can be attached. An example of such a device is described in U.S. Pat. No. 6,607,475, the disclosure of which is incorporated herein by reference in its entirety, including any drawings.

Figure 2:
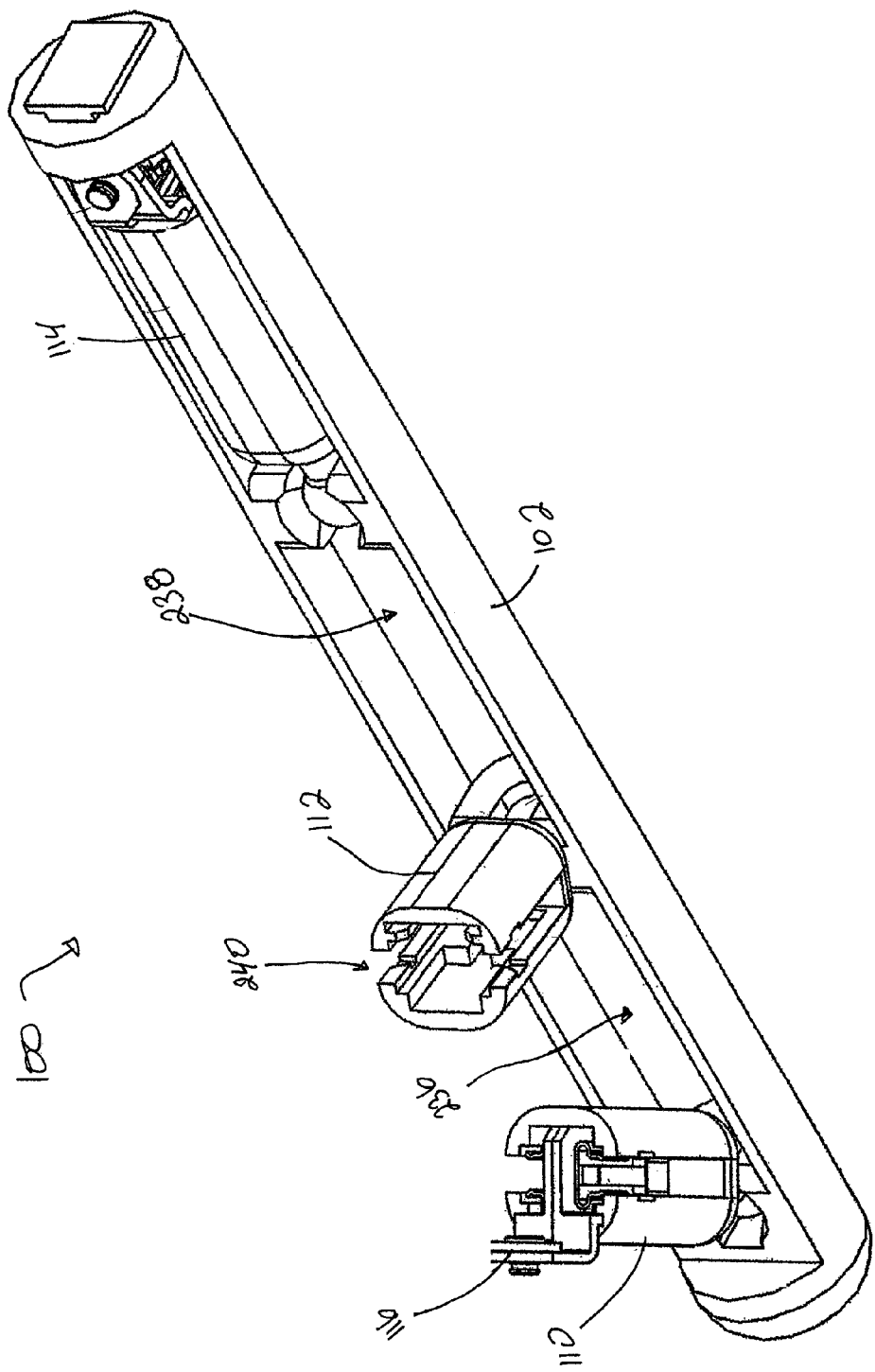
FIG. 2 is a perspective view of the tool kit wherein the holster is pivoted outwardly.

In some embodiments, when the operator wishes to use a certain tool inside a generally closed or confined area, after the operator has inserted the manipulator and a tool kit 100 within that area, the operator can pivot a tool holder 110 around the hinge, created by the combination of the attachment element 122, 126, 130 and the attachment point 124, 128, 132, to an extended position, thereby exposing the tool 116 attached thereto. An example of this embodiment is depicted in FIG. 2. A first tool holder 110 and a second tool holder 112 are shown pivoted outwardly in an extended position. The first tool holder 110, which houses a tool 116, is pivoted for removing the tool 116 and attaching it to a manipulator, while the second tool holder 112 is pivoted outward to receive a second tool. The manner by which tools are attached to, and detached from, the manipulator is explained in detail below. It is understood that if there is no tool attached to the manipulator, there would typically be no need to pivot an empty tool holder 112 outward. Furthermore, it is understood that the angle by which a tool holder is extended is dependent on the angle of approach of the manipulator, and not dependent on whether a tool is being retrieved from, or replaced in, the tool holder.

Referring still to FIG. 2, housing 102 can include openings 236 and 238 in which tool holders 110 and 112, respectively, are positioned in their resting position. In the particular embodiment shown in FIG. 2, tool holder 114 is depicted in its resting position. The tool holders 110 and 112 can be adjusted away from the housing and openings 236 and 238 when needed for interchanging tools. FIG. 2 also illustrates the opening 240 provided in tool holder 112 for receiving a tool.

Each tool kit can include one, two, three, four, five, or more tools. In some embodiments, the tool kit comprises a plurality of tools. The tool includes an attachment element for attaching the tool to a tool receiving device, as described herein. The tools can have different shapes and sizes, depending on the particular application. In some embodiments, the tools are disposable. Disposable tools are particularly desirable in medical applications. In other embodiments, the tools can be used repeatedly. In some of these embodiments, it would be necessary to clean, and sometimes disinfect or sterilize, the tools in between uses.

Figure 3:
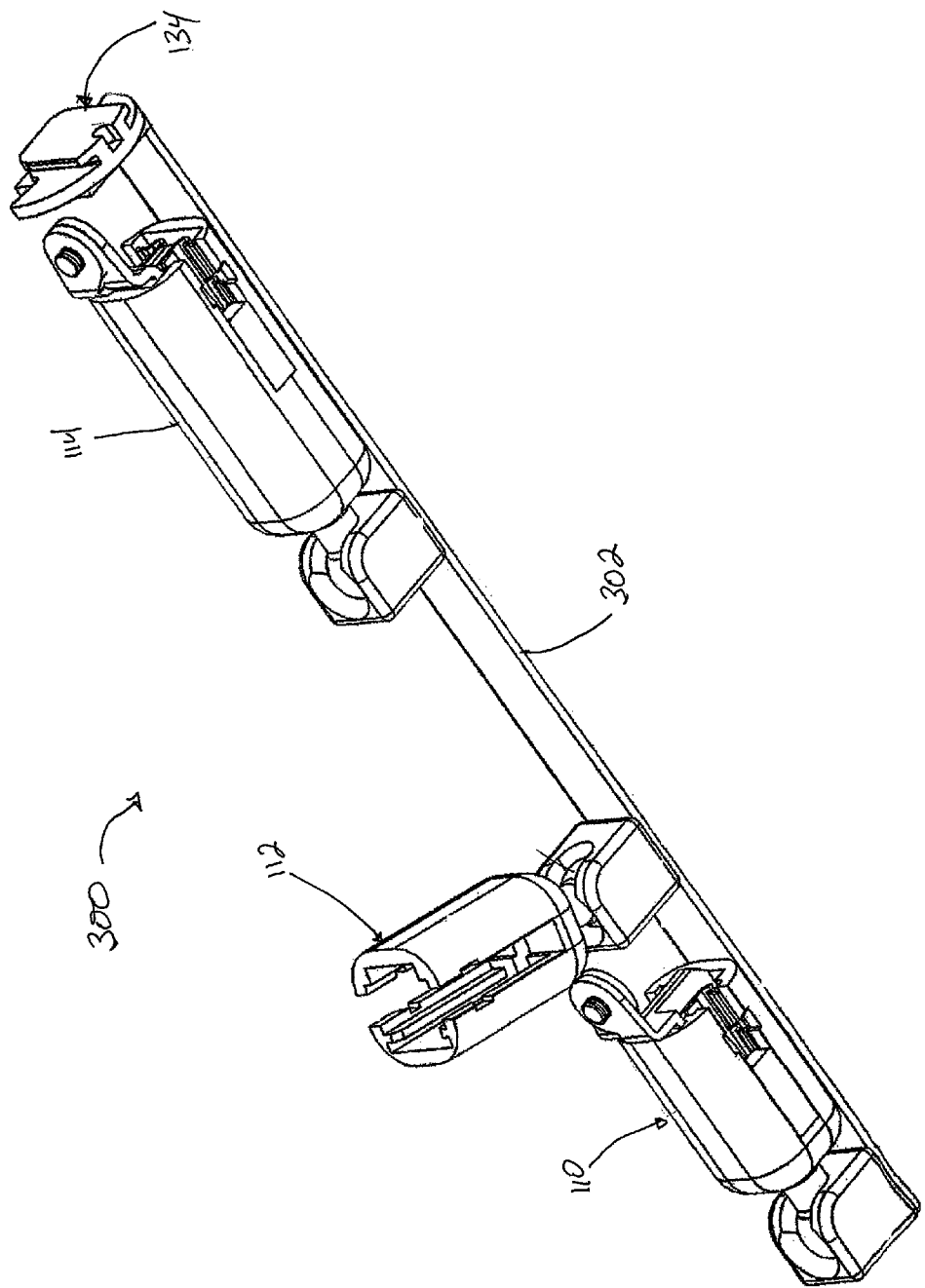
FIG. 3 is a perspective view of an alternative embodiment of a tool kit in accordance with one embodiment of the present invention.

Another embodiment of the tool kit 100 is shown in FIG. 3. In this alternative embodiment, instead of a housing 102, which encases the tool holders, tool kit 300 comprises a spline 302 to which the tool holders 110, 112, 114 are attached. The spline 302 allows the tool kit 300 to be bendable or formable, thereby easing insertion into the confined space and making the tool kit 300 more accessible in a plurality of locations, specially those that are harder to reach. The spline 302 can be formed from any variety of materials, such as metals, plastics, wood, rubber, and the like. A particular material used for spline 302 is determined by the particular application for which the tool kit 300 is used.

In one embodiment, one tool kit is provided in the generally closed area. In other embodiments, a plurality of tool kits are provided in the generally closed area. In some embodiments, two, three, four, five or more tool kits are provided in a closed area. In some embodiments, a number of different tool kits can be attached to the same cannula, whereas in other embodiments, only one tool kit is attached to each cannula.

Figure 4:
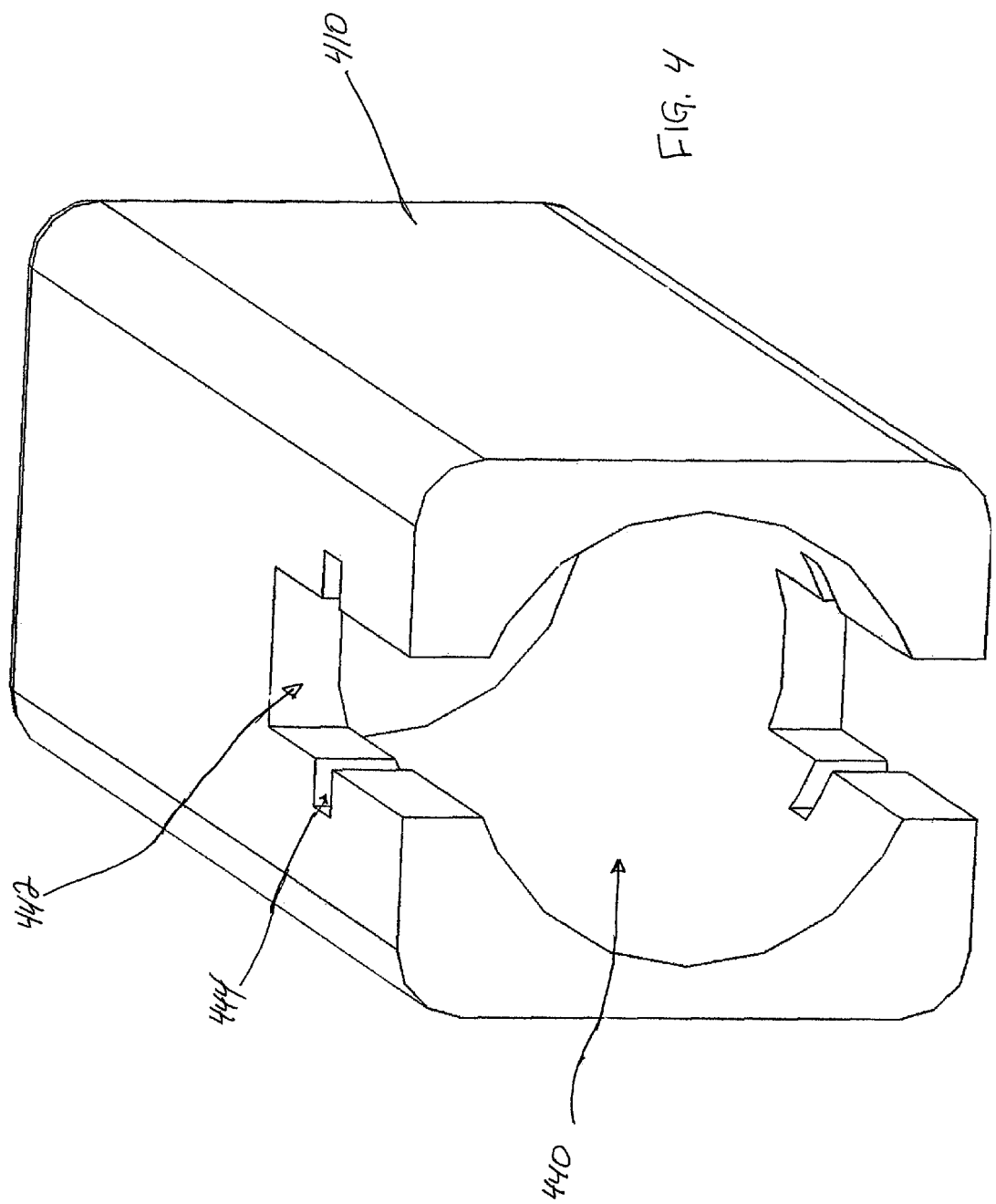
FIG. 4 is a detailed perspective view of the tool holder.

In FIG. 4, a detailed perspective view of an embodiment of a tool holder 110 is shown. The tool holder 410 includes an opening 440. The opening 440 also can include a keyway 442 on at least one of its sides. In some embodiments, the keyway 442 is provided on at least two sides of the opening 440. The keyway 442 can also include a slot 444. As described below, keyway 442 and slot 444 may be used to releasably lock the tools within opening 440 of the tool holder 410.

In some embodiments, the tool holders 110, 112, 114 are shaped to securely hold a specific tool, thereby preventing tools from being incorrectly inserted into a holder belonging to another tool. The tools described herein can be constructed in such a way that the base of the tool, i.e., the proximal portion of the tool closest to the tool receiving device, has a particular shape, such as cylindrical, cubical, conical, frusto-conical, and the like. Each tool holder 110, 112, 114 is also designed to have an opening having a shape corresponding with the shape of one of the tools. Thus, a tool having a cylindrical base would fit into a tool holder 110 having a cylindrically-shaped opening. Likewise, a tool having a cubical base would fit into a tool holder 110 having a cubically-shaped opening, and so on. The opening 440 in FIG. 4 is shown as being generally cylindrical for receiving a tool having a generally cylindrically-shaped base.

Other means for creating a one-to-one relation between the tool holder 110 and a tool are also contemplated. In some embodiments, the location of the keyway 442, for example its distance from the edge of the tool holder 410, or the shape and/or size of the keyway 442, for example its depth or width, is configured to correspond to the location, shape, and/or size of a component on the tool that fits through the keyway 442. The tool holders are preferably semi-rigid, and, in some embodiments, flex somewhat to permit insertion of the tools into the tool holders.

Method of Interchanging Tools

A method for interchanging tools within a closed area is described below. While each step of this method is described in detail below, the general outline of this method is as follows. In one embodiment, an operator selects the desired tools and loads them onto a tool kit, making sure each tool is securely held by a tool holder. The tool kit is then inserted into a closed area. Following the insertion of the tool kit into the closed area, the operator, using the manipulator, can adjust the tool holders outwardly away from the tool kit and into an extended position to allow the operator to easily exchange the tools within the closed or confined area. As described below, each tool can be removed from and reattached to the tool holder of the tool kit as desired. The operator exchanges tools by inserting or placing the tool currently being used into its appropriate tool holder and picking up another tool from another tool holder with the tool receiving device. The tool holders can be provided on the same tool kit or on a separately provided tool kit within the closed area.

The system described herein is designed such that once a tool is placed inside a tool holder, the tool cannot be removed therefrom unless the tool is properly secured and held by the tool receiving device. In addition, once a tool is attached to the tool receiving device, the tool cannot be released from the tool receiving device unless the tool is properly inserted into the tool holder.

Figure 5:
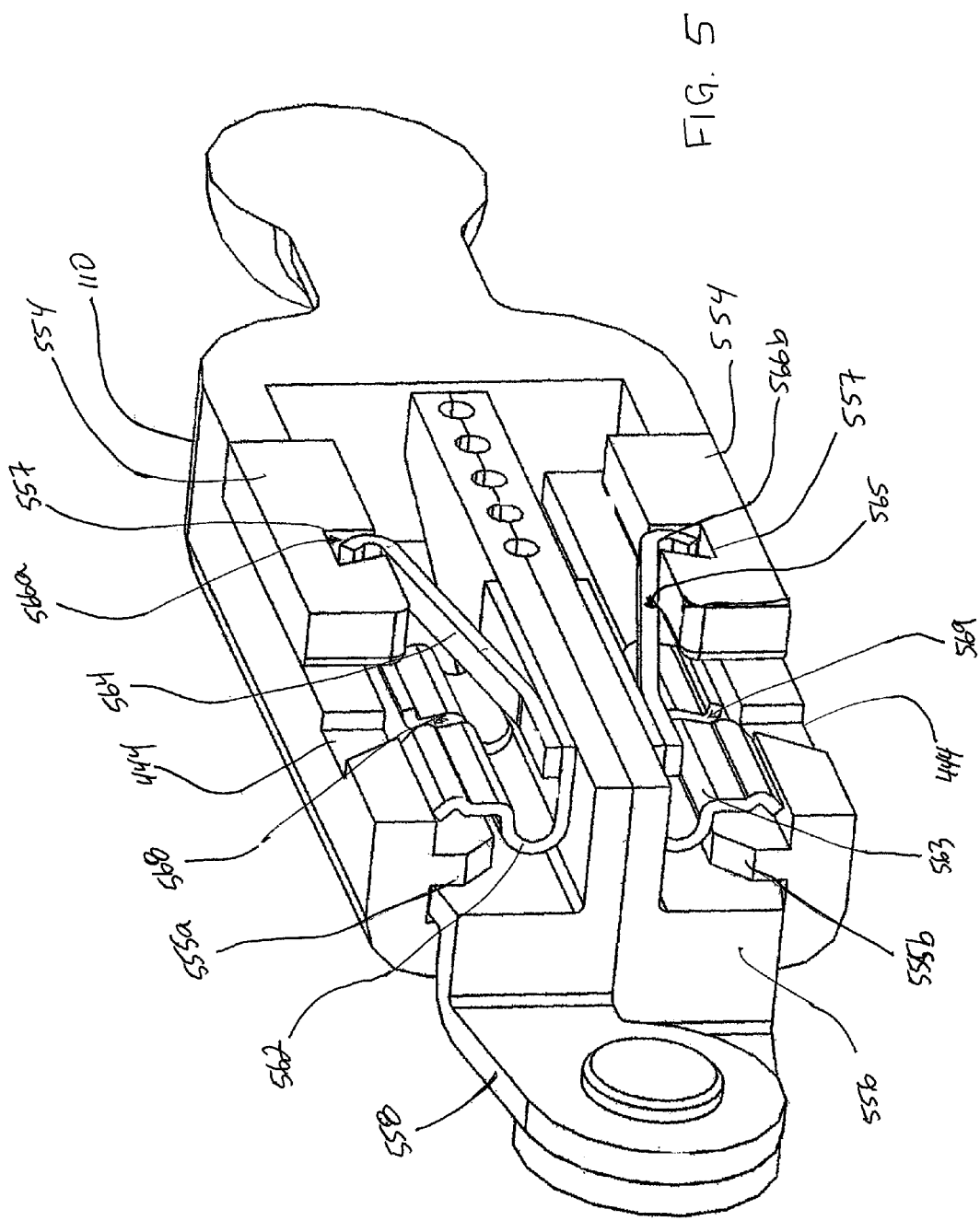
FIG. 5 is a cross-sectional view of a tool held inside a tool holder.

Particular embodiments of the steps of attaching a tool to a tool receiving device and releasing a tool to a tool holder will now be described in detail. FIG. 5 is a cross-sectional view of a tool 556 held inside a tool holder 110. In this particular embodiment, the tool 556 is a clamp. However, it is envisioned that any other type of tool can be used, as described herein. Projections 555a,b prevent the tool 556 from making any lateral movements within the tool holder 110. Each tool 556 is equipped with at least one releasing tine 564. In the particular embodiment shown in FIG. 5, the tool 556 is equipped with two releasing tines 564, 565. The releasing tines 564, 565 exhibit ends 566a,b which curve away from the tool 556.

In some embodiments, the releasing tines 564, 565 exhibit spring-like action, so that in their resting state, i.e., when no external force is applied to them, the releasing tines 564, 565 stay in an "up" position, i.e., a position where the ends 566a,b are located away from the tool 556. The releasing tines 564, 565 in FIG. 5 are shown in their up position. When the tool 556 is placed inside the tool holder 110, the curving ends 566a,b of the releasing tines 564, 565 fit within openings 557 on the tool holder 110, thereby preventing the tool 556 from moving in or out of the tool holder 110.

As a consequence of the projections 555a,b, described above, and the fitting of the releasing tines 564, 565 within the opening 557, the tool 556 remains securely placed inside the tool holder 110.

Figure 6:
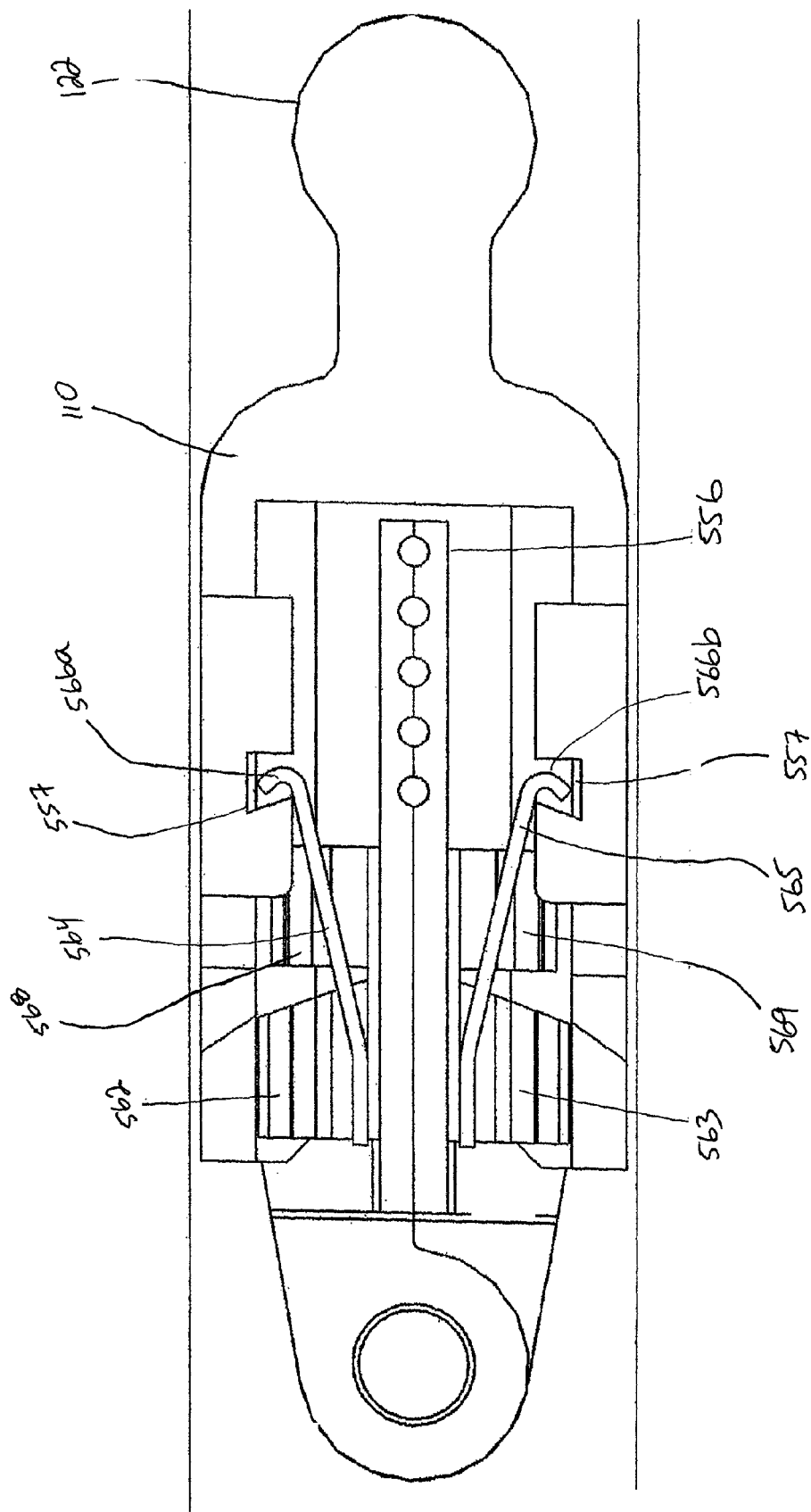
FIG. 6 is another cross-sectional view of a tool inside a tool holder.

FIG. 6 is another cross-sectional view of the tool 556 inside the tool holder 110, showing clearly the curving ends 566a,b of the releasing tines 564, 565 within the opening 557. In some embodiments, such as the one depicted in FIG. 6, the back portion of the opening 557, i.e., the end away from the attachment element 122, is slanted forward, i.e., towards the attachment element 122. This slant, coupled with the curving ends 566a,b of the releasing tines 564, 565, further operates to keep the tool 556 securely held within the tool holder 110.

Figure 7:
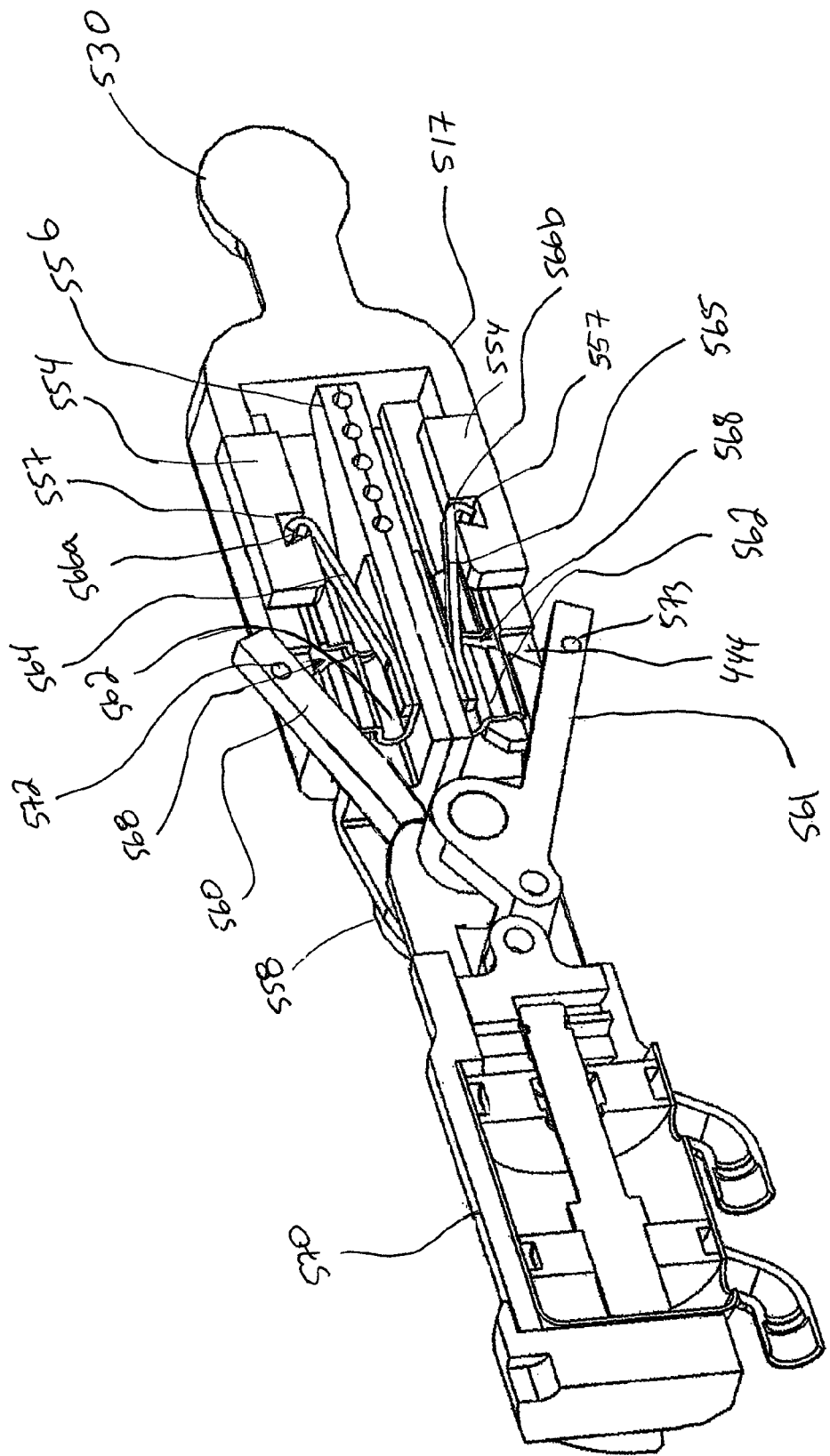
FIG. 7 shows a tool receiving device about to remove a tool from a tool holder.

A tool receiving device is used to remove the tool 556 from the tool holder 110. An embodiment of this process is shown in FIG. 7. This particular tool receiving device 570 exhibits at its distal end a pair of tines 560, 561. In some embodiments, the tines 560, 561 are operated by hydraulic means, such as the methods described in U.S. Pat. No. 6,607,475. The tines 560, 561 can open and close in a scissors-like fashion.

Figure 8:
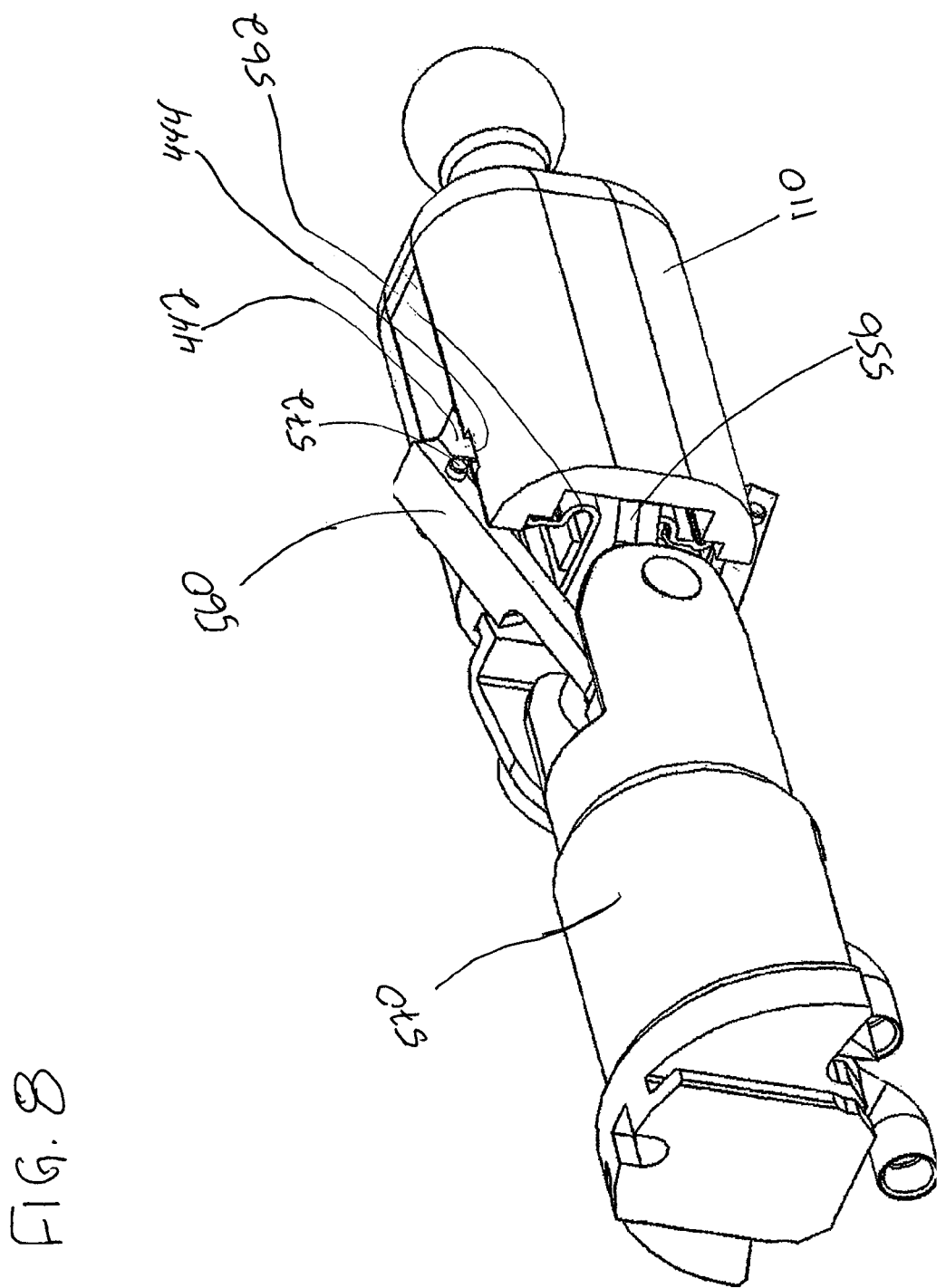
FIG. 8 provides another view of the tool receiving device placed before a tool holder to attach to the tool.

Each tine 560, 561 exhibits a pin 572, 573 at a place substantially close to its distal end. To attach a tool 556 to the tool receiving device 570, an operator opens the tines 560, 561, lines up the pins 572, 573 on the tines 560, 561 with the corresponding slots 444 on the tool holder 110, and then closes the tines 560, 561 such that the tines 560, 561 enter the tool holder 110 through the keyway 442 of the tool holder 110, shown in FIG. 4. The relative positioning of the pins 572, 573 and the slots 444 assure that the tines 560, 561 are properly aligned with the tool 556. FIG. 8 provides another view of the tool receiving device 570 properly aligned with a tool holder 110 so that the pins tines 572, 573 are properly aligned with the slots 444, and tines 560 are poised to enter the tool holder 110 through the keyways 442 to attach to the tool 556.

Turning back to FIG. 5, the tool 556 is equipped with at least one, and in some embodiments two, and in further embodiments more than two, clip elements 562, 568. The particular embodiment shown in FIG. 5 depicts a tool 556 which exhibits two clip elements on each side of the tool 556: a proximal clip element 562, 563 and a distal clip element 568, 569. As shown in FIG. 5, and again in FIG. 6, there are two proximal clip elements 562, 563, one above the tool 556 and one below the tool 556. Similarly, there are two distal clip elements 568, 569, one above the tool 556 and one below the tool 556. The distal clip elements 568, 569 are held back, i.e., away from the releasing tine 564 and towards projection 555, by the cam 554.

When the tines 560, 561 enter the tool holder 110 through the keyway 442, as shown for example in FIGS. 7 and 8, they push the proximal clip elements 562, 563 away from the releasing tines 564, 565 and towards the projection 555. In the embodiment shown in FIG. 5, the proximal clip element 562, 563 is curved at the top, thereby allowing the tines 560, 561 to slide easily down and push the clip element 562 out of the way. The pins 572, 573 on the tines 560 fit in between the two clip elements 562, 568. When the tines are fully closed, through spring-like action the proximal clip elements 562 move back to their original position, thereby causing the tool 556 to be held to the tines 560, 561. At the same time, the releasing tines 564, 565 are pushed flush against the tool 556, i.e., in a position in between the tines 560, 561 and the tool 556. Consequently, the curving end 566 of the releasing tines 564 is no longer inside the opening 557. The operator can now remove the tool 556 out of the tool holder 110 by retracting the distal end of the manipulator.

Figure 9:
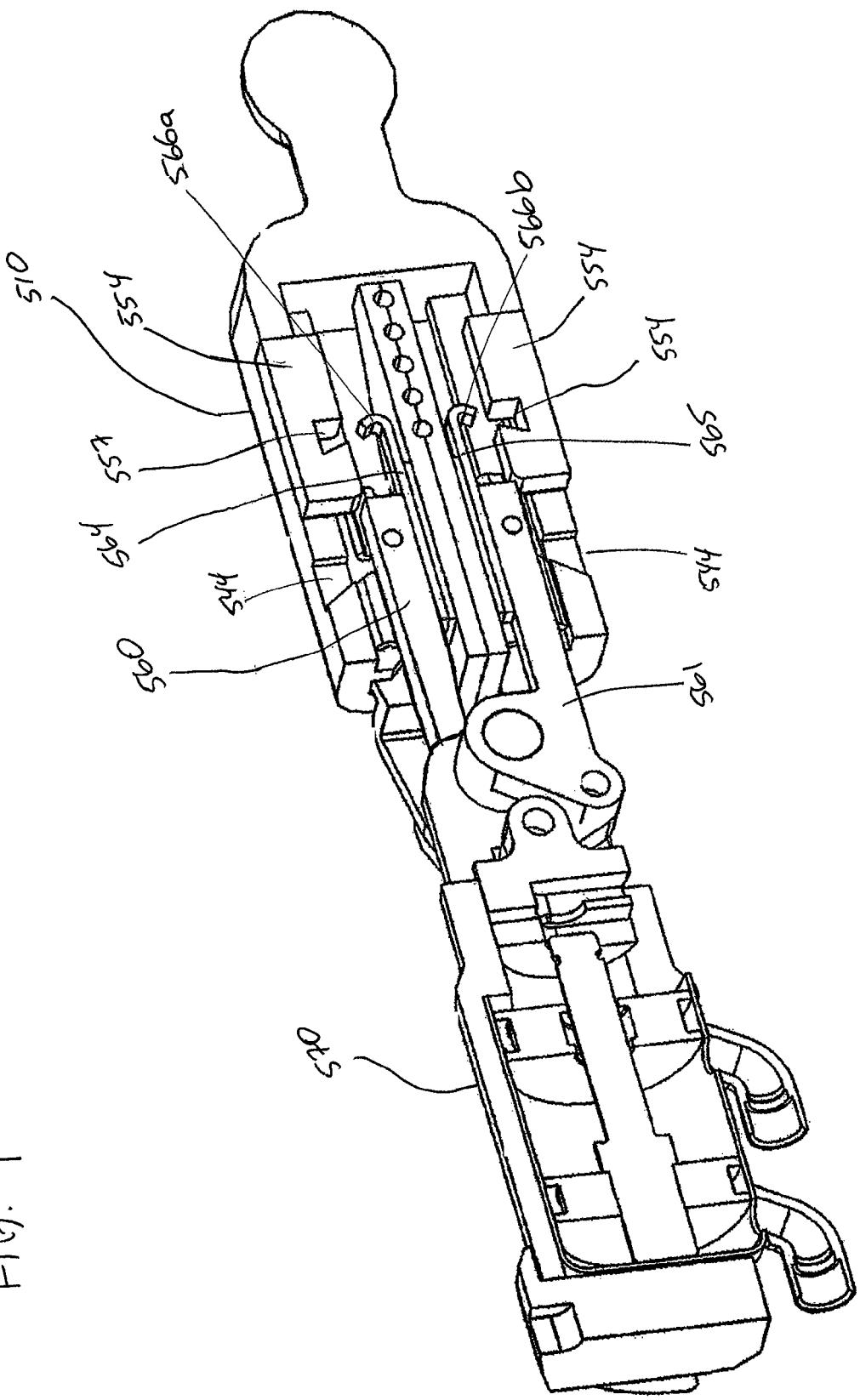
FIG. 9 shows an embodiment in which the tines are closed and the tool is ready to be moved out of the tool holder.

FIG. 9 shows an embodiment in which the tines 560, 561 are in a closed position and the tool 556 is ready to be moved out of the tool holder 110. As shown in this figure, the releasing tines 564, 565 are in their retracted position, i.e., securely held between the tines 560, 561 and the tool 556, and the curving ends 566a,b are outside of the opening 557. The operator now pulls back in a proximal direction on the tool receiving device 570 and removes the tool 556 from the tool holder 110. As the tool moves out of the tool holder 110, the distal clip elements 568, 569 become free from the cam 554, and through spring-like action return back into their resting position, which further secures the tool 556 to the tines 560, 561. As noted in FIGS. 5 and 11, the distal clip elements 568, 569 are curved towards the tines 560, 561 at the top, as opposed to the proximal clip elements 562, 563, which are curved away from the tines 560, 561 at the top. The curvature of the distal clip elements 568, 569 in these particular embodiments provides a more secure hold between the tines 560, 561 and the tool 556.

It is noted that FIGS. 5-9 are cross sectional views. There are corresponding clip elements on the side not shown as well. The end result of the action of all of the clip elements is that the tool 556 will not be able to move laterally with respect to the tines 560, 561. In addition, because the pins 572, 573 fit in between the proximal and distal clip elements, the tool 556 will also be prevented from moving forwards or backwards with respect to the tines 560, 561. Consequently, the tool 556 is securely attached to the tines 560, 561.

Once the operator has used the tool as desired, the operator may wish to change the tool for another tool. The operator then returns the tool currently attached to the tool receiving device to the tool holder, releases the tines, and obtain another tool from another tool holder.

Figure 10:
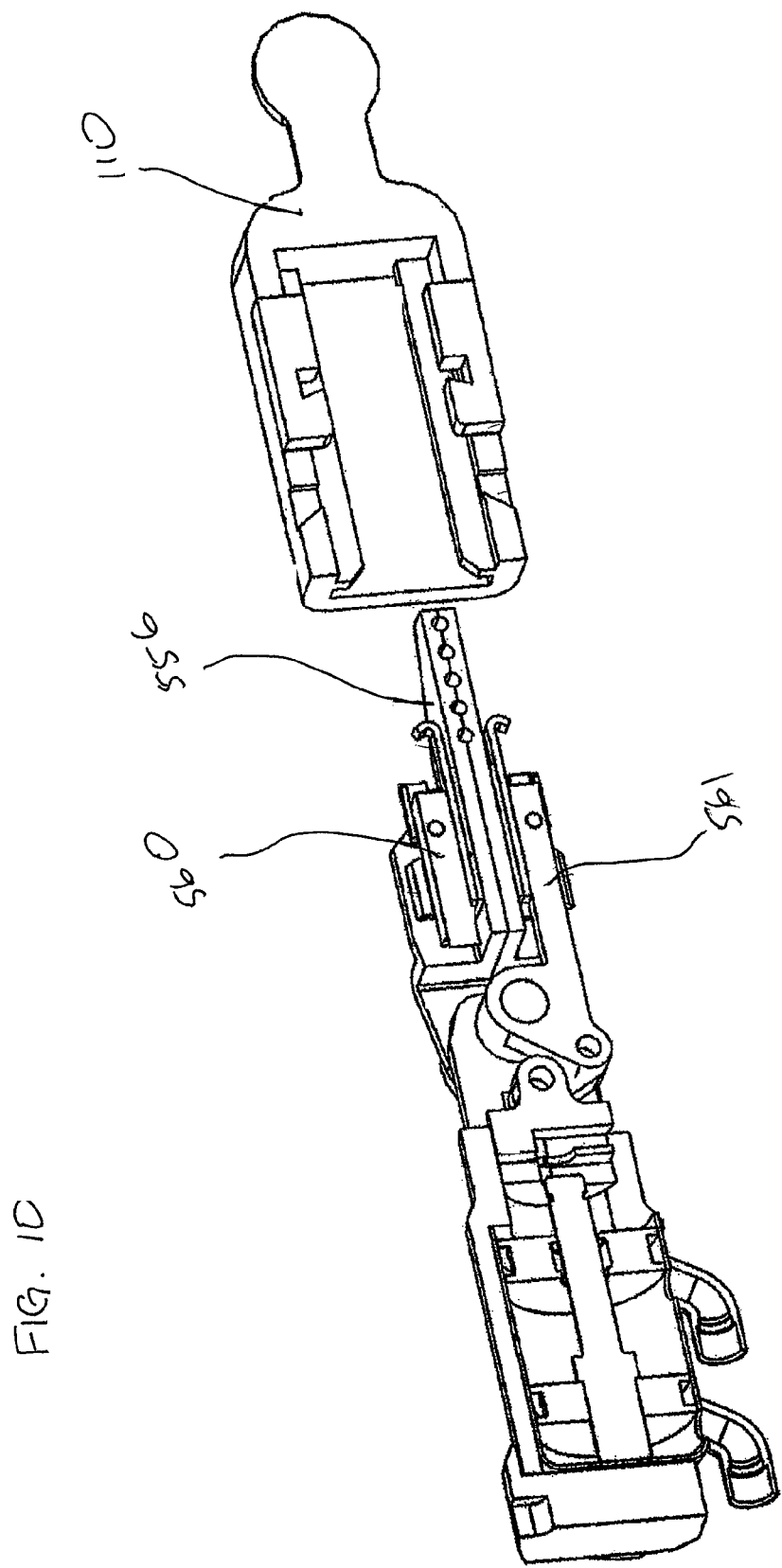
FIG. 10 shows an embodiment in which the tool is attached to the tines of the manipulator and is removed from the tool holder.

In one embodiment, as shown in FIG. 10, to return the tool 556 to the tool holder 110, the operator closes the tines 560, 561, aligns the tool 556 with the tool holder 110, and then moving the tool 556 in a distal direction, inserts the tool 556 inside the tool holder 110. As shown in FIG. 9, cam 554 is placed at a particular depth within the tool holder 110 so that it stops the tines 560, 561 at the proper place for the tines to open and pins 572, 573 be released through the slots 544.

Figure 11:
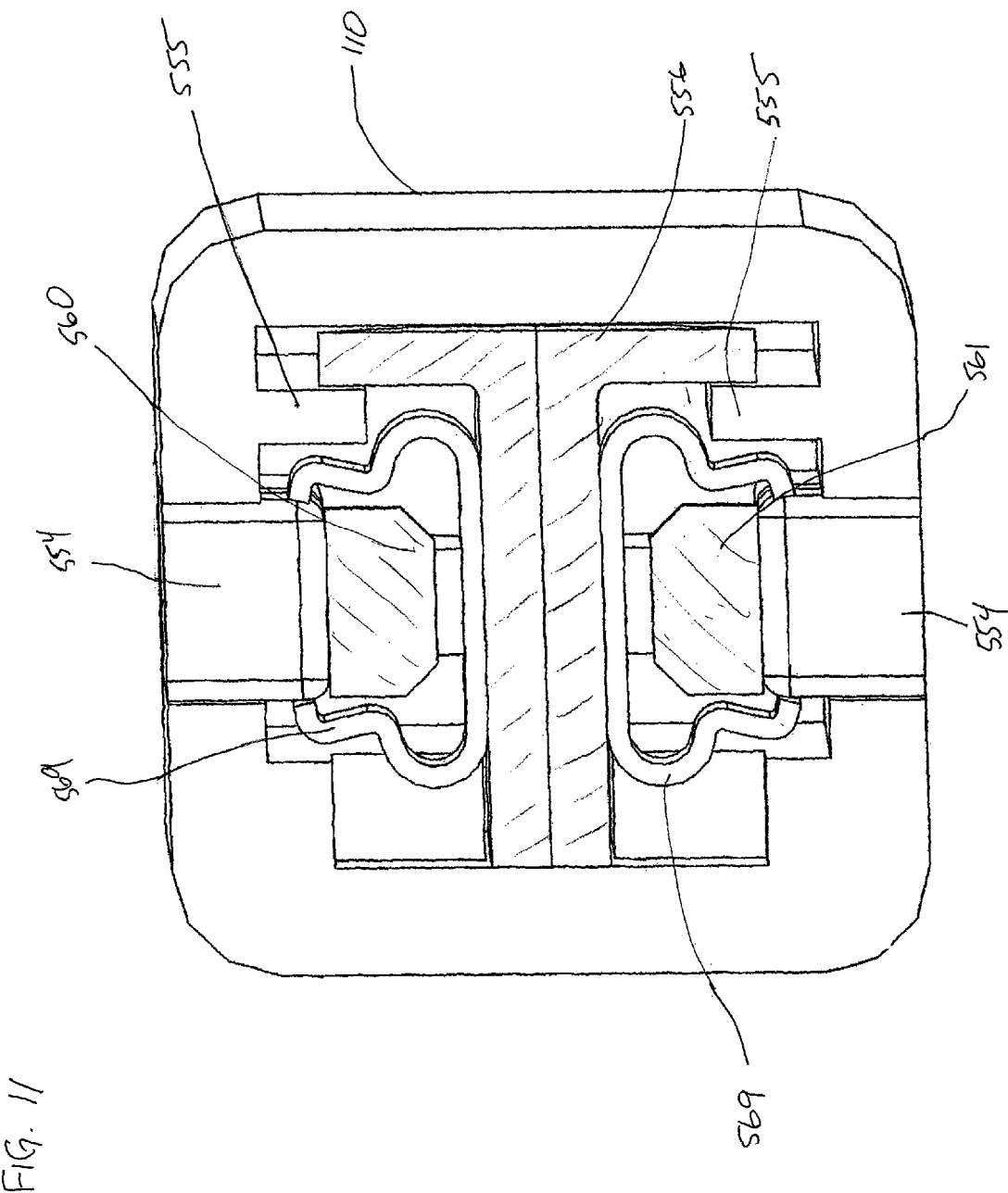
FIG. 11 shows a cross-sectional view of the tool holder with the tool held inside.

In some embodiments, as shown in FIG. 11, cam 554 has curved edges. When the tool 556 is placed inside the tool holder 110 and pushed forward in a distal direction, the distal clip elements 564, 569 come in contact with the curved edges of cam 554. As the tool 556 is pushed further inside the tool holder 110, the curved edges of cam 554 cause the distal clip elements 564, 569 to move backwards, i.e., away from the tines 560, 561. The tool 556 is pushed as far back as it can go inside the tool holder 110. The distal clip elements 564, 569 are now moved completely away from the tines 560, 561.

At this point, the only force holding the tool 556 to the tines 560, 561 is the pressure of the proximal clip elements 562, 563. As seen in FIG. 5, the inside surface of the proximal clip elements 562, 563 is slightly curved away from the tines 560,561 and towards the projections 555a,b. Once the operator opens the tines 560, 561, the proximal clip elements 562, 563 are pushed away from the tines 560, 561, until eventually, the tines 560, 561 snap out of the proximal clip elements 562, 563. As the tines 560 move away from the tool 556, through spring-like action the releasing tines 564, 565 are released and move back to their resting position, which causes the curving end 566 thereof to enter the opening 557, thereby holding the tool 556 securely within the tool holder 110.

As shown in the figures, such as FIGS. 5 and 11, the tool holder 110 includes a shaped channel 570, defined by the wall of the tool holder 110 and the projection 555. The thickness of this channel, i.e., the distance between the projection 555 and the wall of the tool holder 110, can be designed such that a particular tool 556 can fit only into a particular tool holder 110. This feature has the added advantage that the operator can memorize, or label, the position of each tool in a particular tool kit and remain assured that the labeling or the relative positions do not change during the operation of the device.

In other embodiments, the tool 556 is held securely within the tool holder 110 by magnetic force. In these embodiments, each tool holder 110 is capable of being magnetized by the use of electricity. Once the tool holder 110 is magnetized, the tool 556 cannot be removed from the tool holder 110. Once the operator has snapped the tines 560, 561 onto the tool 556, the operator can disengage the electricity flow into the specific tool holder 110, thereby rendering it magnetically neutral. At this point, the tool 556 can be removed from the tool holder 110 by pulling back on the manipulator. In some embodiments, a snap on the tool 556, such as one of the clip elements, can function as a switch, such that when the tines 560, 561 snap into place, the switch is turned off and the tool holder 110 ceases to be magnetized. In further embodiments, the tines 560, 561 can also become magnetized or demagnetized at the command of the operator. Thus, once the tines 560, 561 have snapped onto the tool 556, the operator can demagnetize the tool holder 110 and at the same time magnetize the tines 560, 561. Consequently, the tool 556 can be released from the tool holder 110 and be affixed to the tines 560, 561.

In yet other embodiments, the tool 556 is held within the tool holder 110 by friction. Grooves on both the tool 556 and the tool holder 110 cause enough friction so that the tool 556 does not become loose and fall out of the tool holder 110. However, the amount of friction is small enough to allow the manipulator to remove the tool 556 from the tool holder 110, once the tines 560, 561 are snapped into place.

Surgical Application

In one particularly preferred embodiment, the tool kit is used with a robotic surgical system. An example of a robotic surgery system that can be used with the tool kit is disclosed in U.S. Pat. No. 6,607,475, which is hereby incorporated by reference in its entirety.

In such an embodiment wherein the system for interchanging tools is used in a human body, the tool kit is used with a surgical instrument having a plurality of arms. In some embodiments, the tool kit can be releasably or permanently attached to at least one of the arms of the surgical instrument. In one embodiment, the tool kit is located at the end of an articulating device.

The arm of the surgical instrument is inserted into the closed area through a small opening formed in the patient's body. The tool kit is then positioned and repositioned within the closed area by adjusting the arm of the surgical instrument. Other arms of the surgical instrument can use the tool kit for interchanging tools, so that a plurality of surgical treatments can be performed within the closed area.

The interchangeable tools for use with a surgical instrument can include, but are not limited to, a number of tools for treating a patient, such as irrigation tools, cauterization elements, lead wires, cameras, adhesive application tools, mini-x-ray devices, light sources, and the like. In some embodiments, the tool is a grasper, scissors, blade, optic elements, clamp, marker, and the like. In some embodiments, the tool is ultrasonic cutters, suture drivers, clip drivers, suction/irrigation devices, cauterization devices, needles, catheters, tissue stabilizers, nerve/vessel locators, radiological devices and the like.

Other Embodiments

In some embodiments, a system for identifying particular tools in the tool kit is provided (not shown). In some embodiments, the identification system comprises a color system. For example, the tool holder may be a particular color. In other cases, the tool is also colored and the color of the tool holder and the color of the tool match. Alternatively, words, numbers and/or shapes, and the like may be imprinted on the tool holder or tool kit to identify the location of a tool in the tool holder.

In certain embodiments, the tool kit 100 comprises a cover, which covers the tool holders 110, 112, 114. In some instances, it is beneficial to have the tool holders 110, 112, 114 covered, for example, during the insertion of the tool kit 100 into the closed or confined area, or while removing the tool kit 100 therefrom. Exposed tool holders 110, 112, 114 can have edges that are sharp. In addition, when the tool holders 110, 112, 114 are exposed there exist variations in the circumference of the tool kit 100. These variations and/or sharp edges can cause damage, e.g., tears or nicks, to the small opening through which the tool kit 100 is being inserted into, or retrieved from, the closed or confined area. By utilizing a cover, the tool kit 100 is made to have a uniform and smooth outer layer, which facilitates its insertion and retrieval from the closed or confined area, and within the confined area itself.

In some embodiments, the cover can slide longitudinally along the tool kit 100 to expose the tool holders 110, 112, 114 held inside. In other embodiments, the cover is attached to the tool kit 100 through one or more hinges on one side, and can be moved, e.g., by the operator using the manipulator, to rotate along the hinges into an open position.

In some of these embodiments, the cover is held in the closed position by a latch. The operator would first release the latch prior to opening the cover. The latch further serves the purpose of preventing the cover from opening accidentally while inserting or retrieving the tool kit 100 from the closed or confined area. In further embodiments, once the latch is opened, through spring-like action, the cover moves automatically to the open position, thereby exposing the tool holders 110, 112, 114. Once finished using the tool kit 100, the operator can close the cover, e.g., by using the manipulator, and latch it in the closed position.

In some other embodiments, the cover is moved from the closed to open position, and vice versa, by the use of a remote control device, which sends the necessary signal to a motor in the cover for its operation to open and close through electrical signals that are transmitted through, for example, the cannula, to the tool kit 100, or through radiofrequency waves emitted from somewhere outside of the closed area, or the like.

In certain embodiments, one tool kit 100 is present within the generally closed or confined area, whereas in other embodiments, two or more tool kits 100 are present within the generally closed or confined are. One or more than one manipulator can be present within the same generally closed or confined area, and each of the manipulators can access each of the tool kits 100.

While particular forms of the invention have been described, it will be apparent that various modifications can be made without departing from the spirit and scope of the invention. Accordingly, it is not intended that the invention be limited, except as by the appended claims.

What is claimed is:

1. A surgical kit, comprising:
   a manipulator comprising a tool receiving device;
   at least one tool holder;
   at least one tool adapted to be removably secured to said tool holder;
   wherein said tool is also adapted to be connected to said tool receiving device for use within a generally closed or confined area, and wherein when said tool is connected to said tool receiving device, an operator of said manipulator can exchange said connected tool for a second tool without first removing said tool receiving device from said generally closed or confined area; and
   wherein when said tool is placed inside said tool holder, said tool cannot be removed therefrom unless said tool is properly connected to said tool receiving device, and when said tool is properly connected to said tool receiving device, said tool cannot be released therefrom unless said tool is properly secured into said tool holder.

2. The kit of claim 1, wherein said tool holder is attached to a housing.

3. The kit of claim 2, wherein said housing is configured to hold a plurality of tool holders.

4. The kit of claim 1, wherein said tool is selected from the group consisting of graspers, scissors, blades, screw drivers, drill bits, ultrasonic cutters, suture drivers, clip drivers, suction/irrigation devices, cauterization devices, needles, catheters, tissue stabilizers, nerve/vessel locators, radiological devices, light sources, and cameras.

5. A surgical tool kit, comprising:
   a housing having an opening and at least one attachment point within said opening;
   at least one tool holder having an attachment element, wherein said attachment element is adapted to attach said tool holder to said attachment point in said housing;
   at least one tool adapted to be removably secured to said tool holder;
   wherein said tool is also adapted to be connected to a tool receiving device for use within a generally closed or confined area, and wherein when said tool is connected to said tool receiving device, an operator of said tool receiving device can exchange said connected tool for a second tool without first removing said tool receiving device from said generally closed or confined area; and
   wherein when said tool is placed inside said tool holder, said tool cannot be removed therefrom unless said tool is properly connected to said tool receiving device, and when said tool is properly connected to said tool receiving device, said tool cannot be released therefrom unless said tool is properly secured into said tool holder.

6. The tool kit of claim 5, wherein said tool holder is configured to fit within said housing.

7. The tool kit of claim 6, wherein said housing further comprises a cover for said opening.

8. The tool kit of claim 6, wherein said tool further comprises: at least one releasing tine; and at least one proximal clip element and at least one distal clip element.

9. The tool kit of claim 8, wherein said releasing tine comprises a distal curving end bent away from said tool.

10. The tool kit of claim 9, wherein said distal curving end is configured to fit within an opening on a tool holder when said tool is within said tool holder.

11. The tool kit of claim 8, wherein said releasing tine exhibits spring-like action.

12. The tool kit of claim 8, wherein said releasing tine stays in a position where its distal end is away from said tool when no external force is applied to said releasing tine.

13. The tool kit of claim 8, wherein said proximal clip element and said distal clip element are separated by a distance such that a pin on said tool receiving device can fit between said proximal clip element and said distal clip element.

14. The tool kit of claim 8, wherein said tool comprises two proximal clip elements, one above said tool and one below said tool.

15. The tool kit of claim 8, wherein said tool comprises two distal clip elements, one above said tool and one below said tool.

16. The tool kit of claim 8, wherein said distal clip element exhibits spring-like action.

17. The tool kit of claim 8, wherein said distal clip element is kept at a position towards a projection on said tool holder by a cam on said tool holder.

18. The tool kit of claim 17, wherein said distal clip element returns to its resting position once said tool is removed from said tool holder.

19. The tool kit of claim 5, wherein said attachment element is a generally spherical ball, which fits within said attachment point, which in turn is a socket adapted to receive said attachment point.

* * * * *